(12) United States Patent
Shah (10) Patent No.: US 9,566,059 B2
(45) Date of Patent: Feb. 14, 2017

(54) LAPAROSCOPIC DEVICE FOR ANCHORING AN ORGAN TO THORACIC DIAPHRAGM

(71) Applicant: Rasiklal Shamji Shah, Mumbai (IN)

(72) Inventor: Rasiklal Shamji Shah, Mumbai (IN)

( * ) Notice: Subject to any disclaimer, the term of this patent is extended or adjusted under 35 U.S.C. 154(b) by 99 days.

(21) Appl. No.: 14/406,838

(22) PCT Filed: Dec. 31, 2012

(86) PCT No.: PCT/IN2012/000864
§ 371 (c)(1),
(2) Date: Dec. 10, 2014

(87) PCT Pub. No.: WO2014/061028
PCT Pub. Date: Apr. 24, 2014

(65) Prior Publication Data
US 2015/0157311 A1    Jun. 11, 2015

(30) Foreign Application Priority Data
Oct. 16, 2012    (IN) .......................... 3012/MUM/2012

(51) Int. Cl.
*A61F 2/00*    (2006.01)
*A61F 13/00*    (2006.01)
(Continued)

(52) U.S. Cl.
CPC .............. *A61B 17/0401* (2013.01); *A61B 1/04* (2013.01); *A61B 1/3132* (2013.01); *A61B 17/29* (2013.01);
(Continued)

(58) Field of Classification Search
CPC .............. A61B 17/0401; A61B 1/3132; A61B 17/3468; A61B 2017/00283; A61B 2017/0409; A61B 2017/0417; A61B 2017/0419; A61B 2017/0427; A61B 2017/0464; A61B 2017/3445
See application file for complete search history.

(56) References Cited

U.S. PATENT DOCUMENTS

2004/0102804 A1 * 5/2004 Chin ................ A61B 17/00008
606/190
2004/0138682 A1 * 7/2004 Onuki ................ A61B 17/0401
606/144
(Continued)

*Primary Examiner* — Kristen Matter
(74) *Attorney, Agent, or Firm* — Garrett James O'Sullivan (57) ABSTRACT

Laparoscopic device for anchoring an internal organ to the thoracic diaphragm or abdominal wall of a patient having an introducer sheath; washer with two openings; T-fastener assembly having T-fastener with anchor having a shank with a crown and at least one fluke. The anchor is connected to the T-fastener by a flexible string. A thread is attached to the crown. An introducer needle introduces the T-fastener into a lumen of the internal organ of the patient The device further has a T-fastener pusher inside the introducer needle and locking arrangements for locking the introducer needle and the T-fastener pusher. A blocker blocks the first washer opening and a grasper, inserted through the second washer opening, grasps the shank inside the introducer sheath in a predefined orientation Finally, a holding mechanism on the introducer sheath is provided for holding the grasper in a predetermined position inside the introducer sheath.

16 Claims, 10 Drawing Sheets

(51) Int. Cl.
*A61B 17/04* (2006.01)
*A61B 17/29* (2006.01)
*A61B 1/04* (2006.01)
*A61B 1/313* (2006.01)
*A61B 17/00* (2006.01)
*A61B 17/02* (2006.01)
*A61B 17/34* (2006.01)

(52) U.S. Cl.
CPC ........... *A61B 17/3468* (2013.01); *A61B 90/11* (2016.02); *A61B 2017/00283* (2013.01); *A61B 2017/00477* (2013.01); *A61B 2017/00597* (2013.01); *A61B 2017/00606* (2013.01); *A61B 2017/00818* (2013.01); *A61B 2017/00876* (2013.01); *A61B 2017/0225* (2013.01); *A61B 2017/0409* (2013.01); *A61B 2017/0417* (2013.01); *A61B 2017/0419* (2013.01); *A61B 2017/0427* (2013.01); *A61B 2017/0464* (2013.01); *A61B 2017/3445* (2013.01)

(56) References Cited

U.S. PATENT DOCUMENTS

| | | | | |
|---|---|---|---|---|
| 2007/0185503 | A1* | 8/2007 | Mikkaichi | A61B 17/0469 606/139 |
| 2008/0195126 | A1* | 8/2008 | Solem | A61F 2/24 606/155 |
| 2009/0259260 | A1* | 10/2009 | Bentley | A61B 17/0057 606/300 |
| 2014/0114432 | A1* | 4/2014 | Shalon | A61B 17/0401 623/23.65 |

* cited by examiner

LAPAROSCOPIC DEVICE FOR ANCHORING AN ORGAN TO THORACIC DIAPHRAGM

BACKGROUND OF THE INVENTION

Field of the Invention

The present invention relates to a laparoscopic device for anchoring the internal organs to the thoracic diaphragm or abdominal wall of a patient.

Description of Related Art

The art of laparoscopy has been known to mankind for more than 100 years. However, the rapid growth has occurred in this field only after 1986, when the first laparoscopic cholecystectomy was reported by a surgeon from France. Laparoscopic surgery is one form of surgery carried out by making small incisions on the abdominal wall, instead of the conventional large incisions. It requires using special tubes (called trocars), hand instruments, telescope and camera.

Laparoscopic surgery is performed by making small incisions on the abdominal wall and then inserting several trocars through these small incisions. Thereafter, a telescope is inserted through one of these trocars in order to observe the inside view of the abdominal cavity. Subsequently, through these trocars laparoscopic hand instruments are introduced to be used to manipulate the abdominal viscera in the form of various activities such as—retraction, dissection, cutting, suturing etc. to carry out the laparoscopic surgery. Presently, many laparoscopic surgeries are being performed using this technique. One of the most common surgeries being performed by the laparoscopic technique is cholecystectomy (i.e. removal of the gallbladder for treating symptomatic gallstones).

Normally, laparoscopic cholecystectomy is performed using four trocars. The first trocar is inserted at the umbilicus and the abdomen is filled up with carbon dioxide gas which is pumped in with the help of a pump (called the insufflator). This creates adequate space inside the abdominal cavity for facilitating the surgeon to work inside the abdomen during the laparoscopic surgery. Through this trocar, a telescope is passed which is connected to small camera (called endocamera). This telescope picks-up the image of the inside of the abdominal cavity and displays it on television monitor. Three more trocars are inserted in the abdomen for introducing various laparoscopic hand instruments. The surgeon carries out various surgical steps with these instruments. The position of these trocars varies from surgeon to surgeon and from patient to patient.

The first step of laparoscopic cholecystectomy is passing a grasping forceps through a port on the right side of the abdomen to grasp the fundus (upper part) of the gallbladder and push it towards the thoracic diaphragm. This step exposes an area called "Calot's triangle" region below the liver which carries the cystic artery and the cystic duct entering the gallbladder. Then, the surgeon introduces two more instruments from other two trocars to dissect out the cystic artery and the cystic duct before they are clipped and divided. Dissection of the gallbladder from the liver and its extraction follows to complete the surgical procedure.

A recent modification to the technique of laparoscopic cholecystectomy has been the single incision laparoscopic cholecystectomy. In this form of surgery only one incision is made near the umbilicus and the laparoscope as well as all the instruments are introduced through various trocars placed side by side or a specialized device that accommodates up to three or four instruments. However, one of the instruments is exclusively tied up for the retraction of the gallbladder.

However, in such laparoscopic surgeries, an assistant is continuously required to keep a grasp on the grasping instrument used for retraction of a particular organ, such as gall bladder. At least four trocars are needed to perform such laparoscopic cholecystectomy or any such surgery involving grasping of various internal organs, for operating on them by laparoscopic procedure. Even if the laparoscopic surgery is performed through a single incision, actually there is a shortage of space for inserting multiple devices or tubes for carrying out this surgery. In addition, sometimes a needle-hole grasper is also required to be used in such single incision laparoscopic surgery.

OBJECTS OF THE INVENTION

Some of the objects of the present disclosure, which at least one embodiment herein satisfies, are as follows:

It is an object of the present invention to reduce the number of trocars used in a laparoscopic surgery.

It is another object of the present invention to dispense with the need of an assistant during such laparoscopic surgeries for holding the grasping instrument/s for retraction of an organ.

It is yet another object of the present invention to reduce the cost of such laparoscopic surgeries.

It is a further object of the present invention to increase the space available for each instrument to be introduced inside the abdominal cavity during a single incision laparoscopic surgery.

It is a still further object of the present invention to simplify the procedure by enabling a good retraction and thus to make even a single incision laparoscopic surgery safer by decreasing the incidence of injury to the bile ducts.

It is a yet another object of the present invention to eliminate the need for inserting an additional thin instrument, such as a needle-hole grasper to grasp and retract the organ to be removed during a single incision laparoscopic surgery.

Other objects and advantages of the present invention will be more apparent from the following description when read in conjunction with the accompanying figures of drawings, which are however not intended to limit the scope of the present invention in any way.

BRIEF SUMMARY OF THE INVENTION

In accordance with the present invention, there is provided a laparoscopic device for anchoring an internal organ to the thoracic diaphragm or abdominal wall of the patient, the device comprising: an introducer sheath; a washer closing the outer end of the introducer sheath in a sealing manner; at least one T-fastener and at least one anchor having at least one fluke and a shank; the anchor is connected by means of a flexible string to the T-fastener, the T-fastener assembly disposed inside the introducer needle; and a flexible disc at the junction of the flexible string with the T-fastener and a piece of thread attached to the crown of the anchor; at least one introducer needle for introducing the T-fastener into lumen of the internal organ; at least one T-fastener pusher disposed inside the introducer needle; a locking arrangement disposed for locking the introducer needle inside the introducer sheath; another locking arrangement disposed for locking the T-fastener pusher inside the introducer needle; at least one grasper for grasping the shank of the anchor inside the introducer sheath in a predefined orientation; a holding mechanism provided on the introducer sheath for holding the grasper in a predetermined position inside the introducer sheath; and a blocker to block the opening in the washer.

BRIEF DESCRIPTION OF THE ACCOMPANYING DRAWINGS

The laparoscopic device in accordance with the embodiments of the present invention will now be explained in more detail with reference to the non-limiting accompanying drawings in which.

DETAILED DESCRIPTION OF THE ACCOMPANYING DRAWINGS

The laparoscopic device in accordance with the present invention will now be described with reference to the accompanying drawings, which do not limit the scope and ambit of the disclosure.

The following description of the specific embodiments of the laparoscopic device for anchoring the internal organs to the thoracic diaphragm or abdominal wall of a patient will so fully reveal the general nature of these embodiments that by applying the current knowledge in the art, others can readily modify and/or adapt these specific embodiments for various applications, without departing from the generic concept of the present invention, and therefore, such adaptations and modifications should and are intended to be comprehended within the meaning and range of the equivalents of the embodiments disclosed in the present invention. It is to be understood that the phraseology or terminology employed in this specification is merely for the purpose of description and not for limiting the scope thereof. Therefore, although the embodiments in this disclosure have been described in terms of its preferred embodiments, the skilled person in the relevant art will readily recognize that these embodiments can be applied with modifications within the spirit and scope of the present invention as disclosed and described in this specification.

Figure 1:
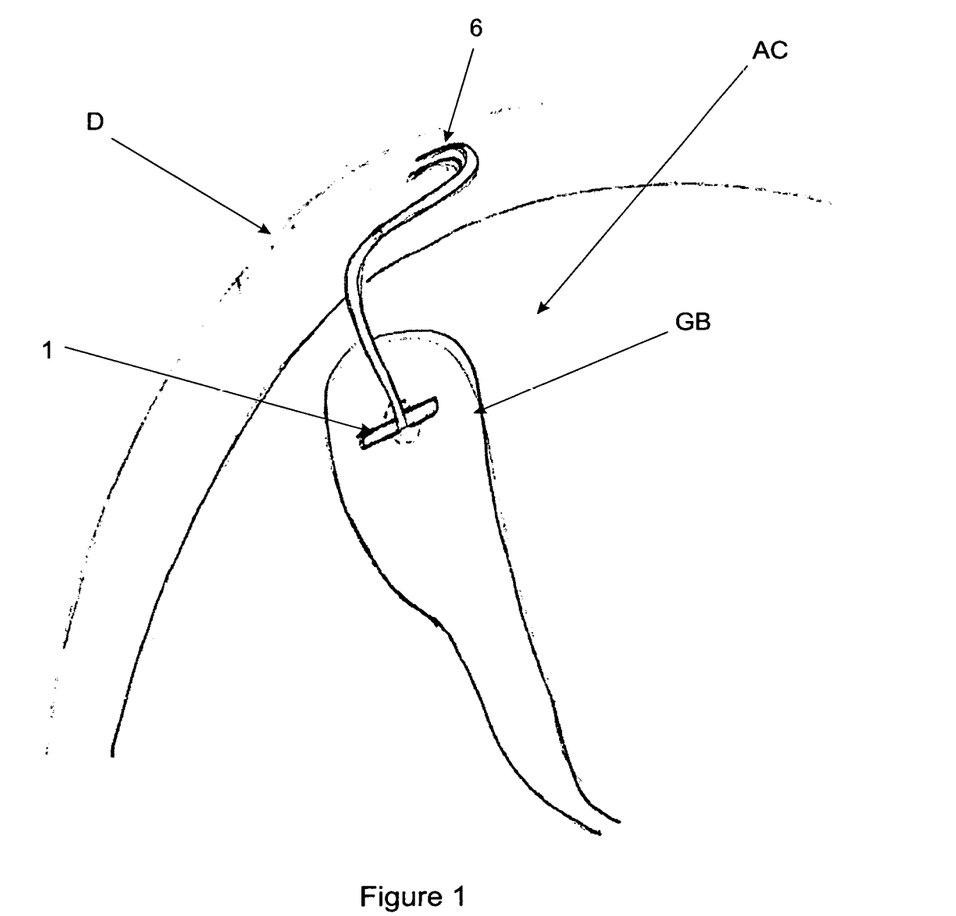
FIG. 1 illustrates an operating region, e.g. abdominal cavity AC showing the gallbladder GB, which is to be pulled by means of a T fastener assembly in accordance with the present invention.

FIG. 1 illustrates an operative region, e.g. abdominal cavity AC showing gallbladder GB which is to be pulled by means of a T-fastener 1 inserted into the lumen of the gallbladder GB. The flukes 6 are of the anchor of the T-fastener assembly are engaged into the thoracic diaphragm D or abdominal wall.

Figure 2:
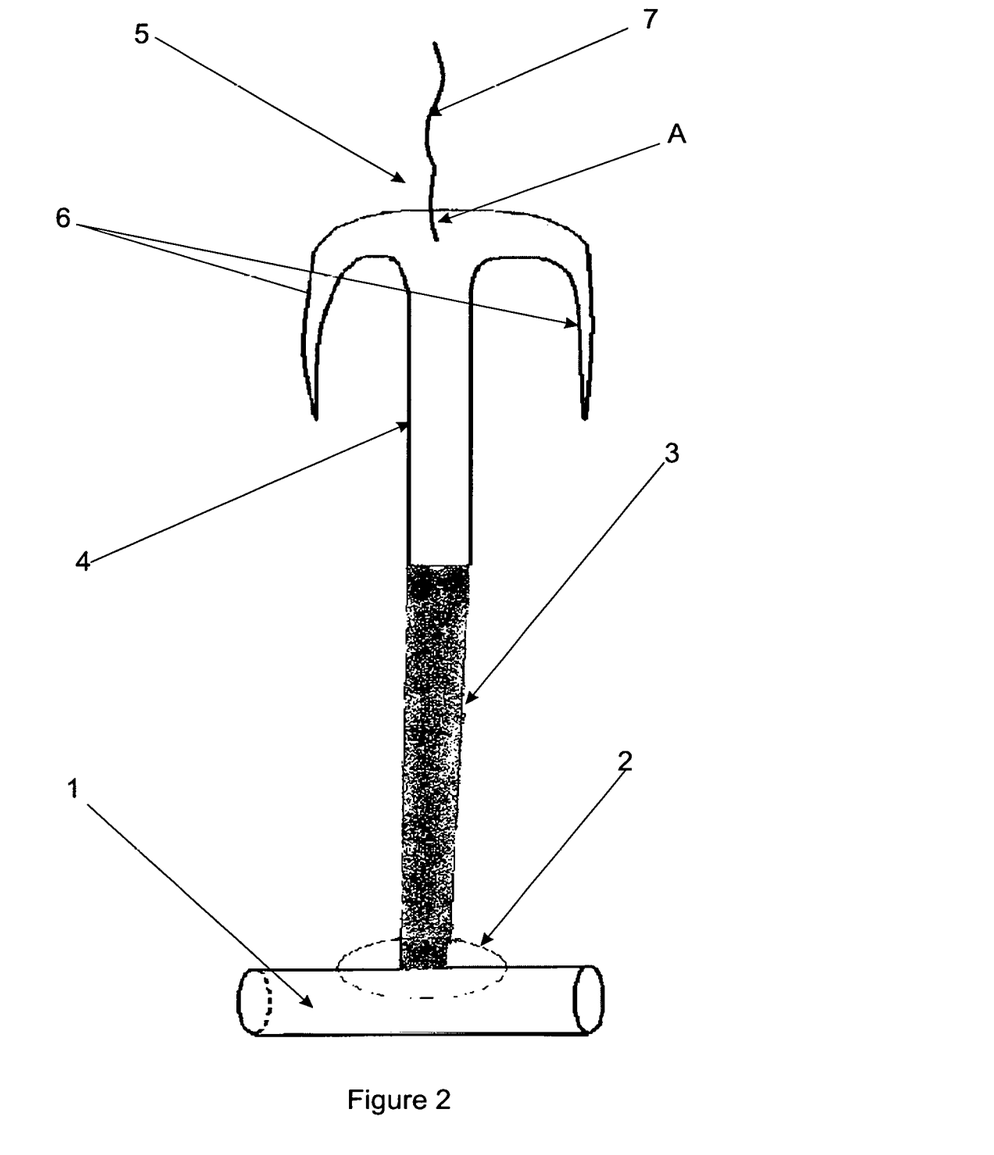
FIG. 2 illustrates a front view of the most preferred embodiment of the T-fastener assembly of the laparoscopic device in accordance with the present invention.

FIG. 2 illustrates a detailed view of the most preferred embodiment of the T-fastener assembly of the laparoscopic device in accordance with the present invention. The T-fastener assembly includes a T-fastener 1 made of a composite material and attached by means of a flexible string 3 to an anchor A having double flukes 6. Although, two flukes 6 are shown in this embodiment, there can also be T-fastener assembly with single or even more than two flukes. The T-fastener 1 has a length substantially longer than its diameter which in turn is slightly smaller than that of the introducer needle in which it is normally housed. The sides of the T-fastener 1 are configured convex to make it blunt to prevent any accidental puncture in the internal organ of the patient. The anchor A has a shank 4, a crown 5 and two flukes 6. The shank 4 is a solid flat cylinder made of metal, plastic or any other suitable material. The shank 4 ends on one side in the crown 5 and on the other side it is fixed with the flexible string 3. The flukes 6 that gently curve back, originates from the crown 5 of the anchor A. The ends of these flukes 6 are sharp enough to allow an easy penetration of and engagement into the thoracic diaphragm D or abdominal wall AC. The flexible string 3 is made up of an elastic or non-elastic material and is fixed to the shank 4 at one end and to the T-fastener 1 at the other end. The crown 5 is attached with another piece of string 7, which is useful for the removal of the anchor A by cutting the string 3 on completion of the laparoscopic surgery; the Anchor A is removed by pulling the piece of string attached to the crown by grasper into the introducer sheath and the detached T-fastener 1 will remain in the gallbladder and is removed along with the gallbladder. The junction of the flexible string 3 with T-Fastener 1 is fitted with a flexible thin disc 2, which seals the opening made in the gallbladder from the inside and thus preventing any leakage of the contents of the gallbladder into the operative region. The size of the T-fastener assembly can be suitably modified, so that it can be introduced through a trocar of suitable size used in laparoscopic surgery. The composite material of T-fastener may preferably include suitable polymers and a magnetic material. This description of the T-fastener assembly has T-fastener 1 at one end and anchor A at the other end. However, if required, it can be suitably modified to have anchor A at both the ends. It can also be modified to have T-fastener 1 at both the ends, which are suitably connected by means of the flexible string 3. In such a case, there can be a plurality of grasper or a plurality of introducer needle along with the respective T-fastener.

Figure 3:
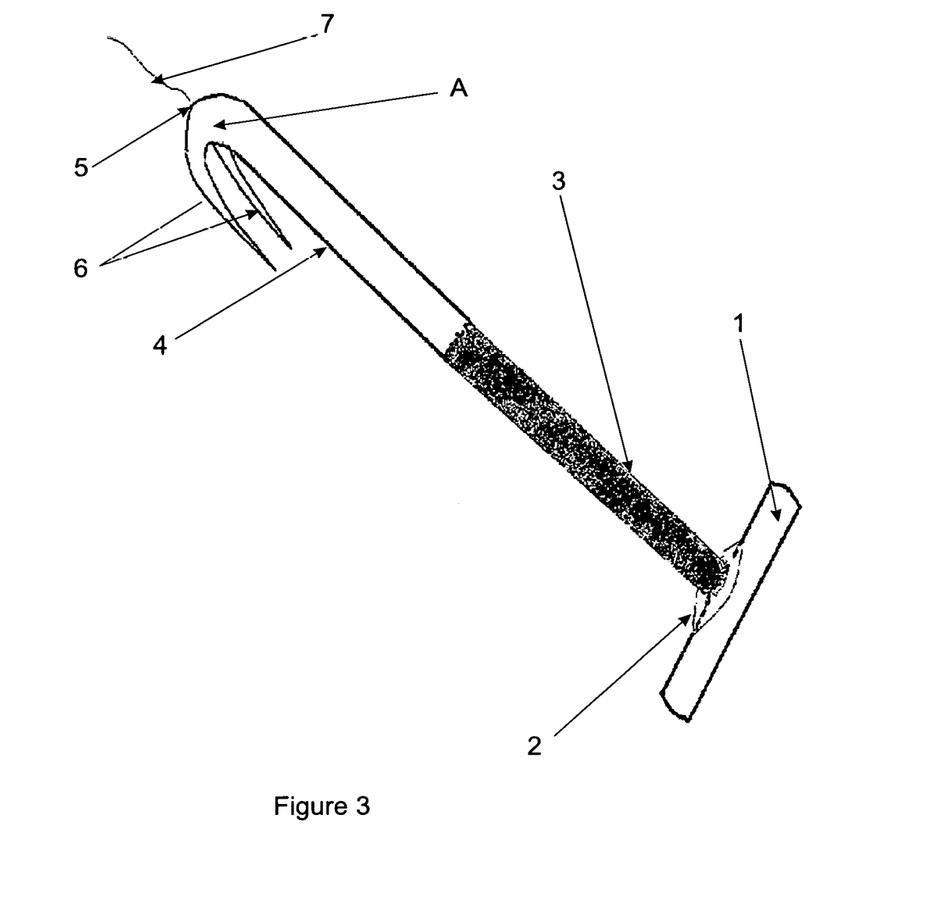
FIG. 3 illustrates a perspective view of the T-fastener assembly shown in FIG. 2.

FIG. 3 illustrates the T-fastener assembly shown in FIG. 2 in a perspective view.

Figure 4:
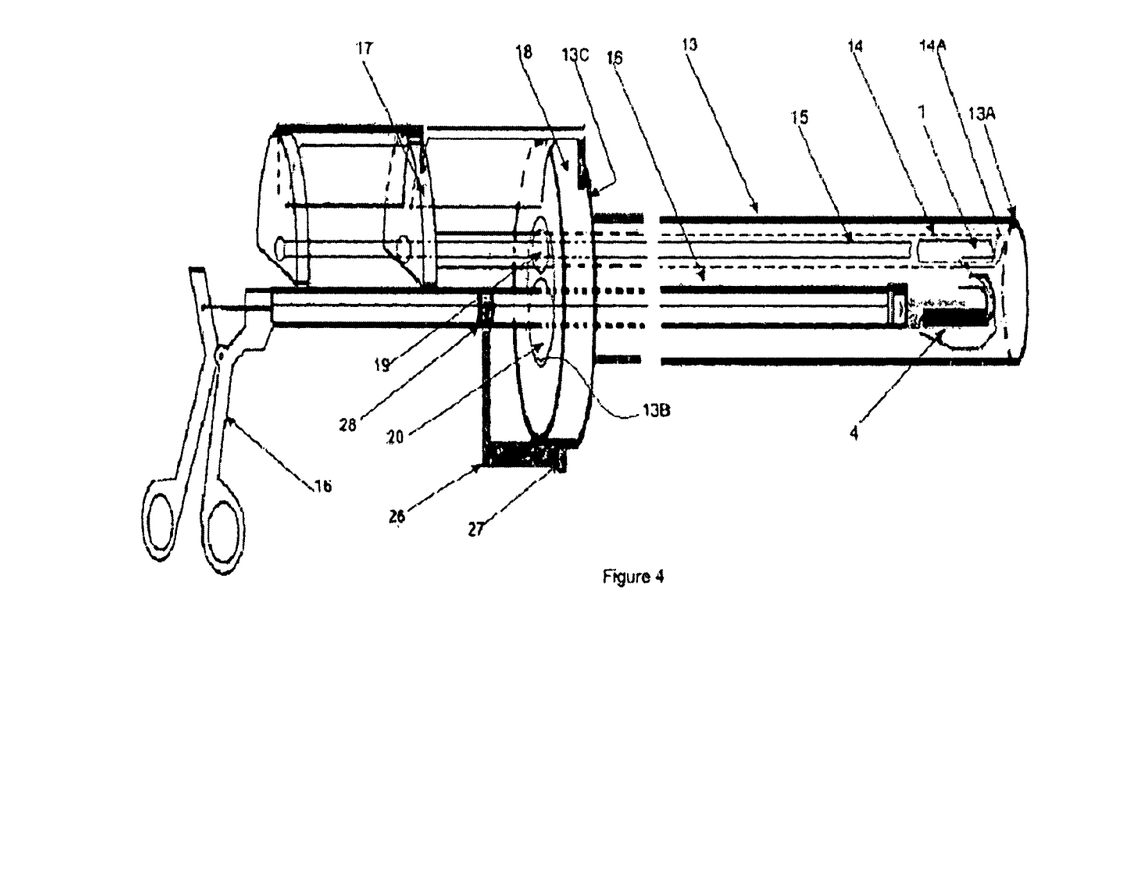
FIG. 4 illustrates a laparoscopic device in accordance with the present invention including an introducer sheath assembly to be inserted into a trocar for delivering the T-fastener assembly into the operative region during a laparoscopic surgery of a patient.
Figure 6:
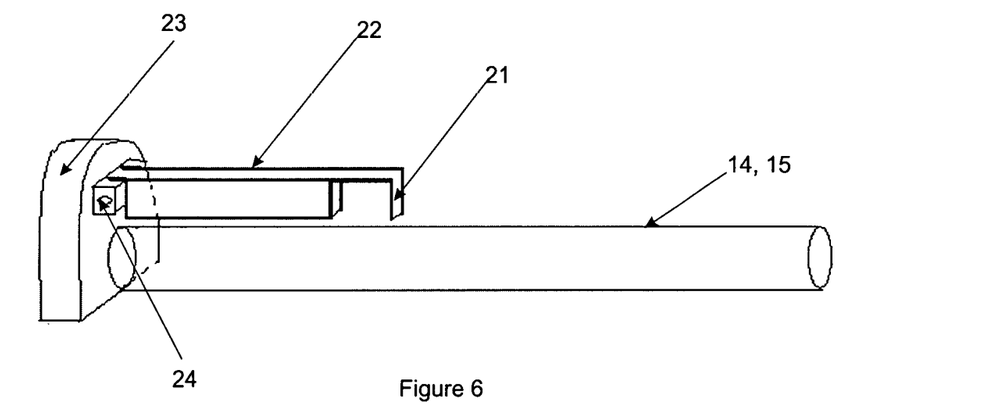
FIGS. 6&7 illustrate a locking arrangement of the pusher assembly for pushing the T-fastener assembly from the introducer needle or for pushing the introducer needle into the operative region of the laparoscopic surgery.
Figure 7:
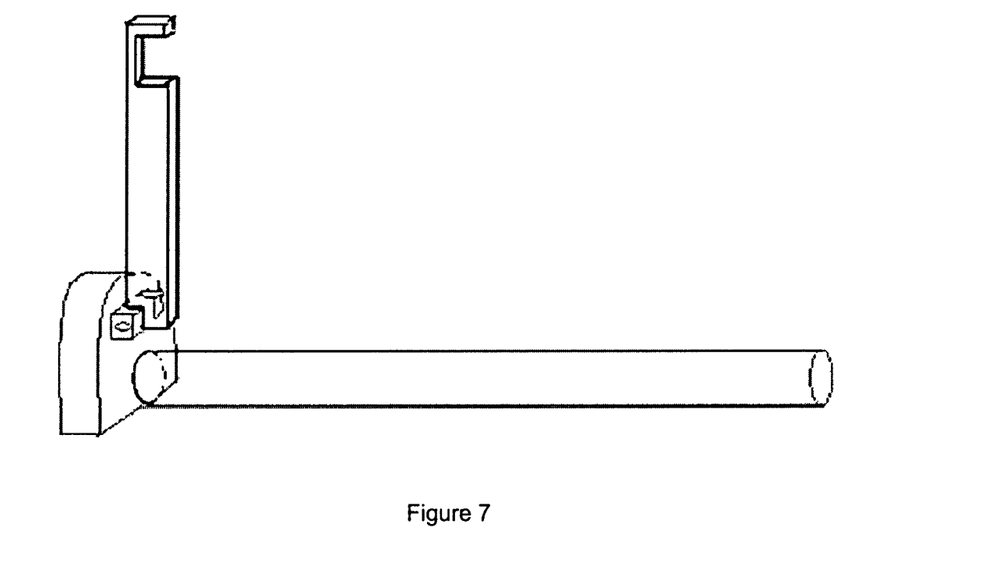

FIG. 4 illustrates the laparoscopic device (henceforth called the Device) in accordance with the present invention. In laparoscopic cholecystectomy, this Device will anchor the fundus of the gallbladder to the thoracic diaphragm D. It shows an introducer sheath 13, which is a hollow tubular structure of adequate diameter to harbor the introducer needle 14 with T-fastener assembly at its inner end 13A as well as the T-fastener pusher 15. The T-fastener 1 is resting inside the sharp tip 14A of the slotted introducer needle 14. A grasper 16 is also provided, which is inserted through the outer end 13B of the introducer sheath 13 for grasping the shank 4 of the anchor A of the T-fastener assembly. The introducer sheath 13 is introduced through a trocar during the laparoscopic surgery. A washer 18 is provided with two respective openings 19 and 20 for insertion of the introducer needle 14 and grasper 16. The outer end of the introducer sheath 13 expands into cylindrical disc 13B, which is covered with the washer 18 snugly fitting over the cylindrical disc 13B of the introducer sheath 13. Through the opening 19 in the washer 18, the introducer sheath 13 accommodates the introducer needle 14 which in turn accommodates a T fastener 1 and the T-fastener pusher 15. The grasper 16 holds the shank 4 of the anchor A of the T fastener assembly for holding the anchor firmly in position inside the introducer sheath. The introducer needle 14 and T-fastener pusher 15 are fitted with a respective locking arrangement for locking and unlocking them inside the introducer sheath and introducer needle respectively, according to the requirements of the laparoscopic procedure at suitable instants and as determined by the surgeon. The hook 21 of the locking arrangement on the introducer needle 14 engages the upper part of the cylindrical disc 13B of the introducer sheath 13. The hook 21 of the locking arrangement on the T-fastener pusher 15 engages the semi-circular flange 17 of the introducer needle 14 (as shown in FIGS. 6 and 7). The washer 18 snugly fits in a sealing manner on the outer expanded cylindrical disc 13B of the introducer sheath 13 and completely seals the openings 19, 20 for the introducer needle 14 and grasper 16 to prevent any leakage of gases around these instruments from the inside of the abdomen. The grasper 16 is used to hold the shank 4 of the anchor A of the T-fastener assembly inside the introducer sheath 13 in a predefined orientation. The holder 26 (shown in FIG. 4) is fixed to the outer expanded cylindrical disc 13B of the introducer sheath 13. The holder 26 grasps the grasper 16 in notches 28 to keep it in a fixed position. The grasper 16 can be released (as determined by the surgeon) by a downward rotation of the holder 26 about the pivot point 27 provided at the lower circumference of the outer expanded cylindrical disc 13B of the introducer sheath 13. If the flukes 6 or T-fasteners are provided on both ends of the anchor A, then the device can be suitably configured to be held in position inside the introducer sheath 13 by the graspers 16 or the introducer needles 14.

Figure 5:
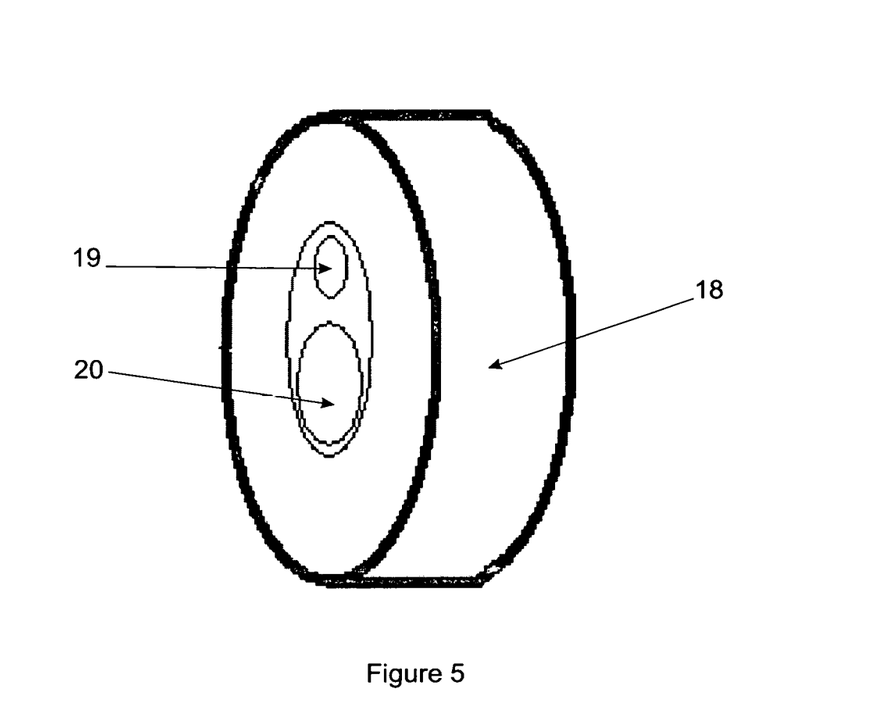
FIG. 5 illustrates a detailed view of the washer of the introducer sheath shown in FIG. 4.

FIG. 5 illustrates a perspective view of the washer 18 of the introducer sheath 13 showing the two respective openings 19 and 20 for the introducer needle 14 and grasper 16. As described earlier, the washer 18 snugly fits over the outer expanded cylindrical disc 13 B.

Figure 5A:
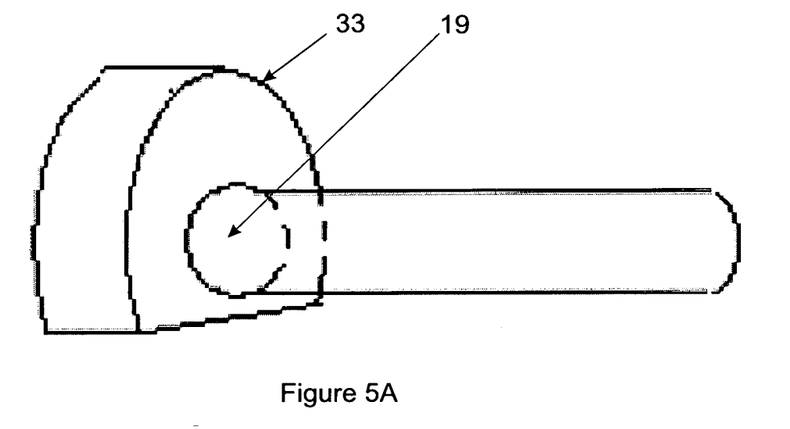
FIG. 5A illustrates the blocker disc for blocking the openings in the washer fitted over the outer end of the introducer sheath shown in FIG. 4.

FIG. 5A illustrates a blocker 33 for blocking the opening 19 after introducer needle 14 is removed from the introducer sheath 13. This is necessary to avoid leakage of gases from the abdomen through the introducer sheath 13. These gases are required to inflate/insufflate the abdominal cavity AC in order to create the working space in the abdomen to carry out the laparoscopic surgery.

FIG. 6 schematically illustrates in detail the locking arrangement of the introducer needle 14 or a T-fastener pusher 15. It shows the locking arrangement in a locked position. This arrangement includes a pivoting mechanism for locking or unlocking the hook 21 of the respective sub-assembly, i.e. the introducer needle 14 or the T-fastener pusher 15. This locking hook 21 is provided on the arm 22, which can be pivoted about a pivot point 24 in a conventional manner to swivel it in locked (horizontal position shown in FIG. 6) or unlocked position (vertical position shown in FIG. 7). The introducer needle 14 is locked to the outer expanded cylindrical disc 13B which is snugly covered by washer 18. Similarly, the T-fastener pusher 15 is locked on the semi-circular flange 23 of the locking arrangement of the introducer needle 14.

FIG. 7 illustrates the same locking arrangement of FIG. 6, however shown in an unlocked position. By releasing the locking hook 21 from the outer expanded cylindrical disc 13B of the introducer sheath 13, it is released for pushing the introducer needle 14 through the wall of the gallbladder GB and into the lumen of the gallbladder GB. Similarly, by releasing the locking hook 21 of the T-fastener pusher 15 from the semi-circular flange 23 of the locking arrangement of the introducer needle 14, the T-fastener pusher 15 is released for pushing the T-fastener 1 into the lumen of the gallbladder GB, which is then to be pulled by means of this T-fastener 1.

Figure 8:
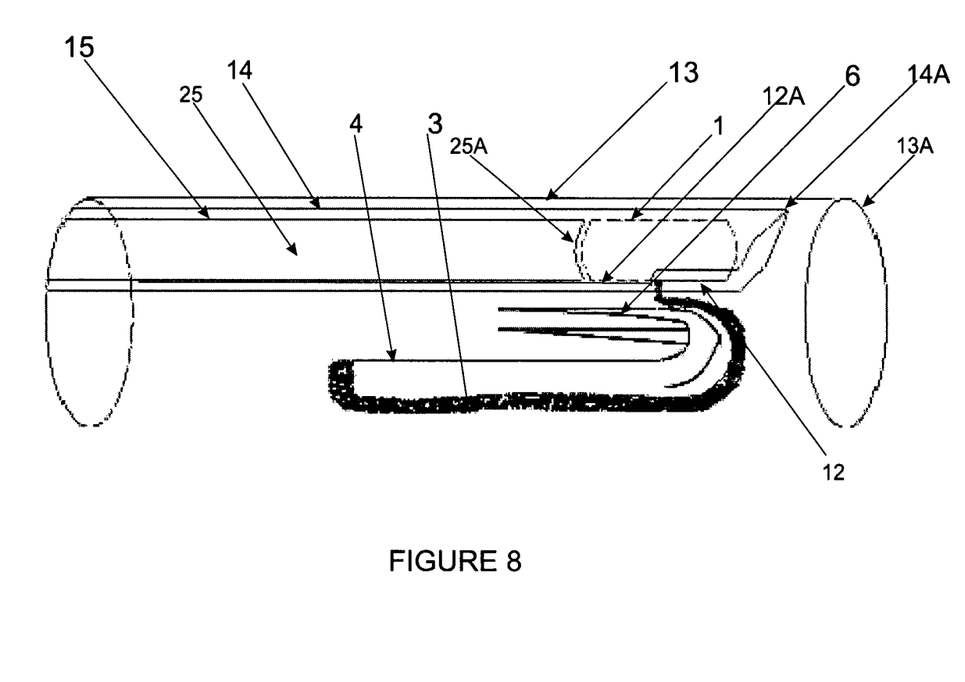
FIG. 8 illustrates the inner slotted end of the introducer sheath showing the position of the T fastener in the introducer needle, the position of the flexible sting emerging out of the slotted end of the introducer needle and position of flukes lying outside the introducer needle but within the introducer sheath.

FIG. 8 illustrates the predetermined position of the introducer needle 14 with the T-fastener pusher 15 inside the introducer sheath 13. In this position, the T-fastener 1 is lying along its length inside the introducer needle 14 and the shank 4 and flukes 6 of the T-fastener assembly are lying outside the introducer needle 14. The T-fastener 1 is connected by means of the flexible string 3 to the shank 4. The T-fastener 1 is kept in this position by means of the magnetic force applied by the magnet 12A fitted about the slot 12 near the inner end of the introducer needle 14 (see FIG. 11). The shank 4 of the T-fastener assembly is grasped by the grasper 16 and kept in a fixed position (not shown). The T-fastener pusher 15 has a long cylindrical tube 25, which has a concave inner end 25A facing the convex side of the T-fastener 1. In its unlocked position, the T-fastener pusher 15 can be withdrawn completely from the introducer needle 14, so that the outer opening 14B (not shown) of the introducer needle 14 has a continuity right up to the tip or inner end 14A of the introducer needle 14 and lumen of the internal organ/gallbladder in which T-fastener 1 has been delivered. Then, the outer opening 14B of the introducer needle 14 can be connected to suction tubing to suck out the contents of the gallbladder in order to reduce spillage of its contents.

Figure 9:
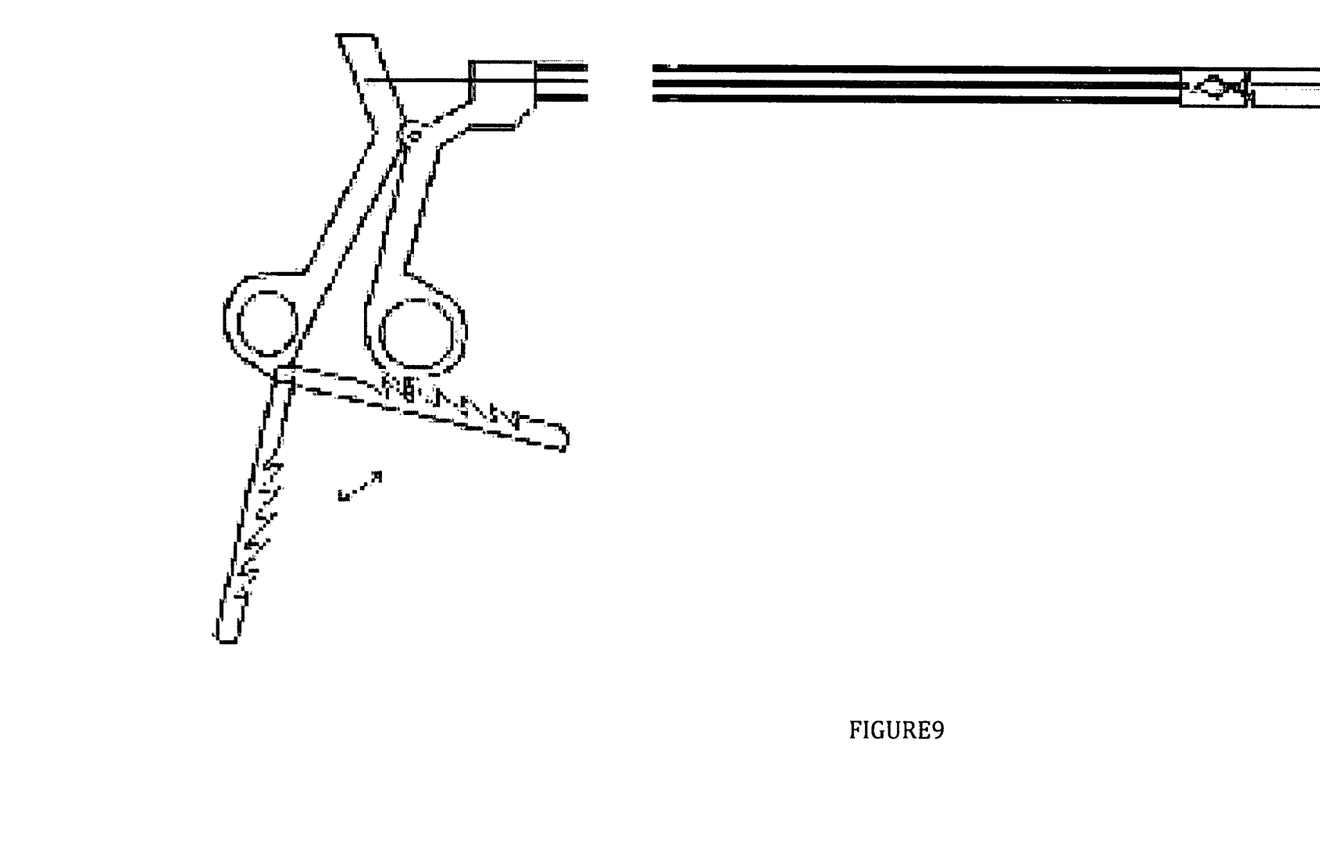
FIG. 9 illustrates another embodiment of the grasper of the grasper assembly shown in FIG. 4.

FIG. 9 illustrates a conventional grasper 16 with grasping jaws 30. The grasper 16 has a locking mechanism provided in the form of notches 28 on the outer surface of the shaft of the grasper 16. These notches 28 are engaged by the locking tabs 29 provided on the holder 26 for the grasper 16 (shown in detail in FIG. 10). The grasping jaws 30 can be locked or unlocked by means of a pawl and ratchet arrangement 31, 32. By means of this mechanism, the shank 4 of the T-fastener 1 (not shown) can be gripped or released by the grasping jaws 30. The two headed arrow 34 shows the direction of movement of ratchet arm 31 for engaging or disengaging with the pawl 32 provided on the handle of the grasper 16.

Figure 10:
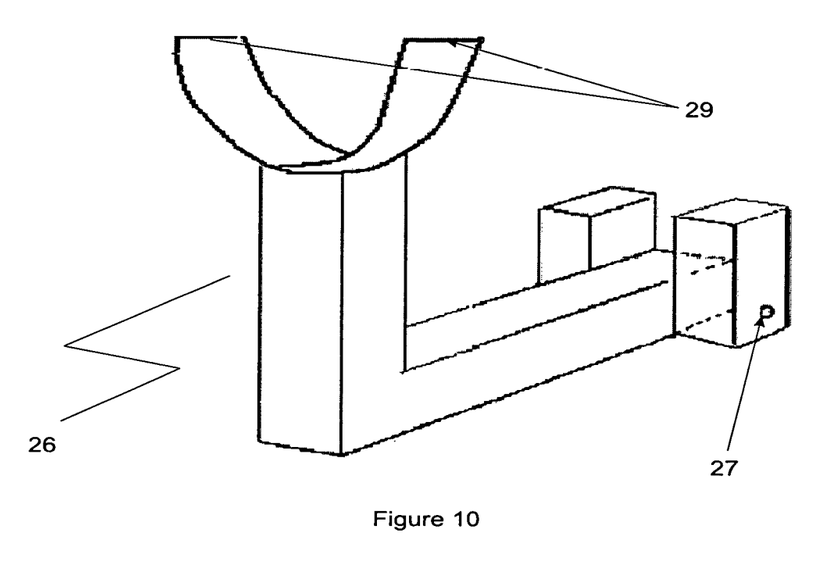
FIG. 10 illustrates an enlarged view of the locking arrangement for the grasper assembly shown in FIGS. 4 and 9.

FIG. 10 illustrates an enlarged schematic view of the holder 26 for the grasper 16. This holder 26 is meant to engage the notches 28 provided on the outer surface of the grasper 16, by means of locking tabs 29. The holder 26 pivots about a pivot point 27 to lock the grasper 16 by means of locking tabs 29 into the notches 28 provided on the grasper 16. Therefore, the shank 4 of the T-fastener assembly is held in position by the grasping jaws 30 of the grasper 16 (see FIG. 9). A plurality of notches 28 are provided at a specific location on its outer surface. The position of these notches 28 are configured such that the T-fastener assembly is held in its locked position near the slotted inner end 13A of the introducer sheath 13. Here, T-fastener assembly, introducer needle 14 with T-fastener pusher 15 and the grasper 16 are all kept housed within the introducer sheath 13.

Figure 11:
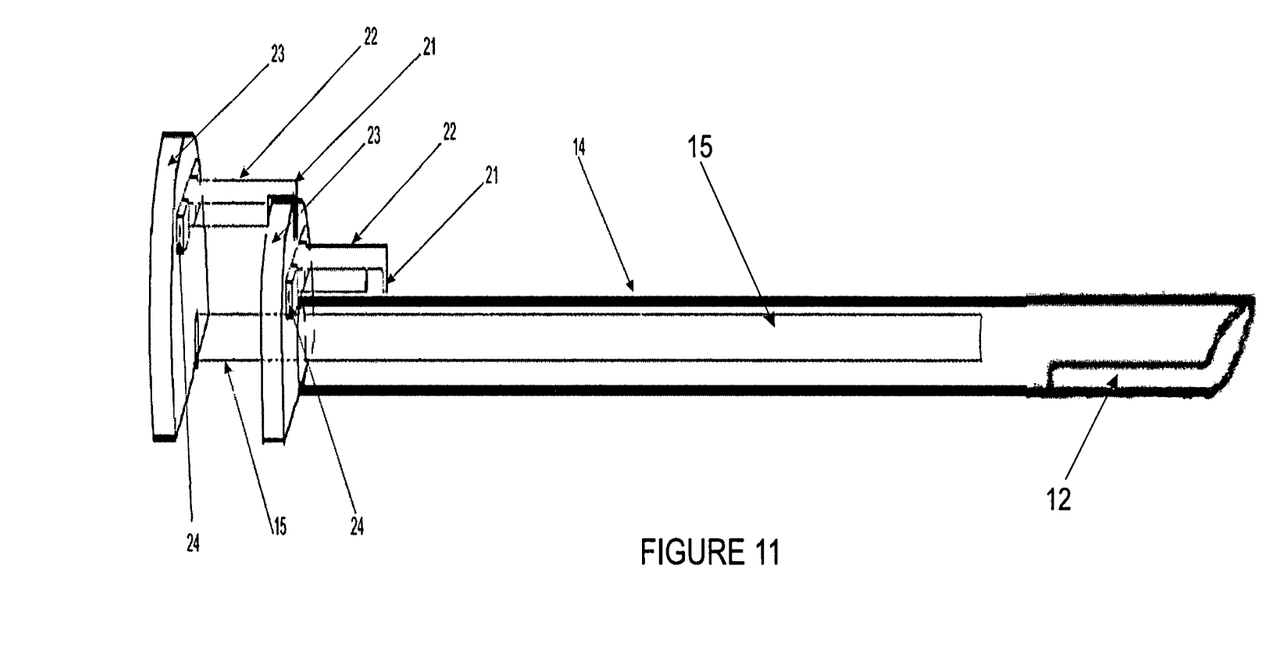
FIG. 11 illustrates an introducer needle (with T-fastener assembly locked inside, not shown) and the T-fastener pusher locked inside the introducer needle.

FIG. 11 illustrates a detailed view of the introducer needle 14 to be inserted in the introducer sheath for delivery of the T fastener assembly of the laparoscopic device in accordance with the present invention in the operative region. On releasing the hook 21 from the outer expanded cylindrical disc 13B of the introducer sheath 13, the introducer needle 14 can be inserted past the inner end 13A thereof, through the wall and into the lumen of the gallbladder. Subsequently, by releasing the hook 21 of the T-fastener pusher 15, the T-fastener 1 can be delivered into the lumen of the gallbladder or any desired internal organ of the patient.

The description provided above is purely by way of example and illustration. In accordance with the present invention, the various features and advantageous details are explained with reference to the non-limiting embodiments in the following description. Descriptions of well-known components and processing techniques are omitted so as to not unnecessarily obscure the embodiments described in this specification.

The examples used herein are intended merely to facilitate an understanding of the various manners in which these embodiments may be used and to further enable the skilled person in the relevant art to practice these embodiments. Accordingly, these illustrative examples should not be construed as limiting the scope thereof.

Working Principle of the Device

The patient is under general anesthesia. For a standard laparoscopic cholecystectomy, the umbilical, epigastric and midclavicular trocars are inserted. The telescope is introduced from the umbilical trocar for preliminary inspection. Then the telescope is shifted to midclavicular trocar and under its vision, this laparoscopic devise is introduced in to the abdomen.

In case of single incision laparoscopic surgery, after insertion of the port/ports at umbilicus, under the laparoscopic vision the Device is introduced inside the abdomen. Then the inner end of the introducer sheath is brought in contact with the fundus of the gallbladder. The locking hook locked on the outer expanded cylindrical disc of the introducer sheath is unlocked and the introducer needle is pushed past the inner end of the introducer sheath, this will allow the introducer needle to pierce the wall of the fundus of the gallbladder. Then the locking hook locked on the semicircular flange of the introducer needle is unlocked and the T-fastener pusher is released to push the T-fastener held by the magnet about slotted end of the introducer needle past its inner end. By this maneuver the T-fastener is delivered into the lumen of the gallbladder. Then, the T-fastener pusher is removed and the outer end of the introducer needle is connected to a suction apparatus. The bile from the gallbladder is sucked to decompress the gallbladder for its easier handling. In addition, this would also decrease the spillage of the bile in the operating area. This prevention of spillage is further enhanced by the flexible thin disc attached to the flexible string near its junction with the T-fastener. This disc shall effectively close the opening in the gallbladder. The introducer needle is removed after completion of suction of bile from the gallbladder. If there is thick purulent fluid, then one can perform repeated suction and irrigation to remove as much pus as possible. Subsequently, the opening in the washer is sealed by the blocker to prevent the escape of the gas from the abdomen. The next step is to fix the flukes of the anchor with the thoracic diaphragm of the patient. To carry out this step, the introducer sheath of the laparoscopic device is pushed towards the diaphragm and the desired area over the diaphragm is selected for anchoring. Then, the grasper (holding the shank of the T-fastener assembly) is unlocked from the holder and it is pushed out of the introducer sheath towards the diaphragm. With the help of the grasper, the flukes of the T-fastener assembly are engaged in the selected, area of the diaphragm. Now, the jaws of the grasper are opened by disengaging the ratchet of the grasper so that the shank of the Anchor is freed up and the grasper is withdrawn along with the introducer sheath from the trocar. This maneuver shall effectively fix the gallbladder with the diaphragm and which in turn should give good exposure of the Calot's triangle to carry out the dissection and control of the cystic duct and cystic artery. If necessary, the fixation area on the diaphragm can be changed with the help of the grasper. The cholecystectomy is completed as usual. After the gall bladder is separated from the liver fossa, the flexible string of the T-fastener assembly is cut near the gallbladder. The T-fastener remains in the gallbladder and is removed along with the gallbladder. The introducer sheath is introduced along with the grasper through the trocar into the abdomen and the piece of string attached to the crown of the anchor is grasped by the grasper and the anchor is pulled into the introducer sheath. The entire assembly of the anchor, grasper and sheath is withdrawn together. The rest of the procedure is carried out as usual.

Technical Advantages & Economic Significance

In laparoscopic surgeries, an assistant is continuously required to keep a grasp on the grasping instrument used for retraction of a particular organ, such as gall bladder, which is dispensed with by using the laparoscopic device in accordance with this invention.

Normally, at least four trocars are needed to perform laparoscopic cholecystectomy or many such surgeries involving grasping of various internal organs, therefore, by using the laparoscopic device in accordance with this invention, requirement of at least one trocar can be reduced during a laparoscopic surgery.

During a single incision laparoscopic surgery, there is always a shortage of space for inserting multiple devices or tubes for carrying out such laparoscopic surgeries. So, by using the laparoscopic device in accordance with this invention, reducing a trocar means a corresponding increase in the space available for movement of the remaining instruments which are inserted from the umbilicus and thus facilitates the surgeon to carry out such laparoscopic surgeries with more ease.

Moreover, in single incision laparoscopic surgery, sometimes a needle-hole grasper is also used to retract the fundus of the gallbladder. Again, by using the laparoscopic device in accordance with this invention, the need for inserting an additional thin instrument, such as a needle-hole grasper is eliminated.

The use of laparoscopic device in accordance with this invention simplifies the procedure even in a single incision laparoscopic surgery by enabling a good retraction of gallbladder to expose the Calot's triangle, which is pre-requisite for safe laparoscopic cholecystectomy. A good exposure to Calot's triangle decreases the incidence of injury to the bile ducts, which is a very morbid condition leading to hospitalization and overall increase in the expenses for such surgeries.

To sum up, with the use of laparoscopic device in accordance with this invention, the eliminating the need of an assistant, reducing at least one trocar especially or reducing use of the grasper to hold the fundus of gallbladder, especially when the disposable grasper is used, there is a substantial reduction in the overall cost of laparoscopic surgery.

This way, the laparoscopic device in accordance with the invention offers a substantial technical advantage and is therefore also of tremendous economic significance to this art.

Other Uses of the Device

Though the description is for the retraction of the fundus of the gall bladder but the device can be used to retract any other hollow or solid viscera by modifying the end of the anchor and length of the intervening flexible string.

While considerable emphasis has been placed herein on the specific features of the preferred embodiment, it will be appreciated that many additional features can be added and that many changes can be made in the preferred embodiments without departing from the principles of the invention. These and other changes in the preferred embodiment of the invention will be apparent to those skilled in the art from the disclosure herein, whereby it is to be distinctly understood that the foregoing descriptive matter is to be interpreted merely as illustrative of the invention and not as a limitation.

I claim:

1. A laparoscopic device for anchoring an internal organ to the thoracic diaphragm or abdominal wall of a patient, the said device comprising:
    an introducer sheath having an inner end configured for insertion in the abdomen of the patient and an outer end having an expanded cylindrical disc with an aperture in a center thereof;
    a washer fitted on the expanded cylindrical disc of the outer end of the introducer sheath in a sealing manner, the washer having two openings;
    a T-fastener assembly including a T-fastener and an anchor having a shank with a crown configured with at least one fluke curving back therefrom and a piece of thread attached to the crown; the anchor connected to the T-fastener by means of a flexible string; a flexible disc disposed at a junction of the flexible string with the T-fastener; the T-fastener assembly disposed inside an introducer needle, the introducer needle for introducing the said T-fastener into a lumen of the internal organ;
    a T-fastener pusher disposed inside the introducer needle;
    a first locking arrangement for locking the introducer needle inside the introducer sheath;
    a second locking arrangement for locking the T-fastener pusher inside the introducer needle;
    a grasper for grasping the shank of the anchor inside the introducer sheath in a predefined orientation, the grasper including a longitudinal shaft having a pair of handles at an outer end thereof and a pair of grasping jaws at an inner end thereof;
    a holding mechanism provided on the introducer sheath for holding the grasper in a predetermined position inside the introducer sheath; and
    a blocker to block one of the openings in the washer after removal of the introducing needle.

2. The laparoscopic device as claimed in claim 1, wherein the introducer sheath has a hollow tubular structure, the inner end and the outer end of the introducer sheath being open.

3. The laparoscopic device as claimed in claim 1, wherein said introducer needle comprises a sharp needle-like slotted inner end having a longitudinal slot of a predetermined length and an outer end having the first locking arrangement for locking the introducer needle inside the introducer sheath.

4. The laparoscopic device as claimed in claim 3, wherein the T-fastener is inserted inside the introducer needle and the flexible string emerges through the slotted end of the introducer needle to locate said shank and the at least one fluke outside the introducer needle but within the introducer sheath.

5. The laparoscopic device as claimed in claim 3, wherein a magnet is disposed about the longitudinal slot for holding the T-fastener in a longitudinal orientation inside the introducer needle and wherein the anchor is attached with the flexible string lying outside said introducer needle but inside said introducer sheath in a predefined orientation.

6. The laparoscopic device as claimed in claim 1, wherein the anchor has a plurality of flukes.

7. The laparoscopic device as claimed in claim 1, wherein the T-fastener is made of a composite material consisting of polymer and a magnetic material.

8. The laparoscopic device as claimed in claim 1, wherein the flexible string is made-up of an elastic or non-elastic material.

9. The laparoscopic device as claimed in claim 1, wherein the grasper is provided with at least one notch at a predetermined location on an outer surface of the longitudinal shaft thereof.

10. The laparoscopic device as claimed in claim 9, wherein the holding mechanism comprises a holder having a first end pivotable about a pivot point provided on the expanded cylindrical disc and a second free end having at least one locking tab for locking or unlocking the holder into or from the at least one notch provided on the outer surface of the longitudinal shaft of said grasper.

11. The laparoscopic device as claimed in claim 1, wherein the first locking arrangement comprises a first semi-circular flange of the introducer needle and having a first pivoting hook formed on an arm pivotable about a first pivot point on the first semi-circular flange to lock or unlock the first pivoting hook on or from a predefined position of the expanded cylindrical disc of the introducer sheath to lock the introducer needle.

12. The laparoscopic device as claimed in claim 11, wherein the second locking arrangement comprises a second semi-circular flange having a second pivoting hook formed on an arm pivotable about a second pivot point on the second semi-circular flange to lock or unlock the second pivoting hook on or form a predefined position on the first semi-circular flange of the introducer needle to lock the T-fastener pusher.

13. The laparoscopic device as claimed in claim 12, wherein the T-fastener pusher is completely removable from the introducer needle by releasing the second pivoting hook from the first semi-circular flange of the introducer needle.

14. The laparoscopic device as claimed in claim 11, wherein the introducer needle is completely removable from the introducer sheath by releasing the first pivoting hook from the expanded cylindrical disc of the introducer sheath.

15. The laparoscopic device as claimed in claim 1, wherein the pair of grasping jaws grasps or releases the shank by means of a pawl and ratchet mechanism provided on the grasper handles.

16. A laproscopic device for anchoring the gallbladder to the thoracic diaphragm or abdominal wall of a patient, the device comprising:
- an introducer sheath having a hollow tubular structure with an inner end configured for insertion in the abdomen of the patient and an open outer end having an expanded cylindrical disc with an aperture in a center thereof;
- a washer snugly fitted on the aperture of the expanded cylindrical disc of the open outer end of the introducer sheath in a sealing manner;
- a T-fastener assembly including a T-fastener made of a composite material consisting of a polymer and a magnetic material and an anchor having a shank having a crown configured with a plurality of flukes curving back therefrom and a piece of thread attached to the crown; the anchor and the T-fastener connected to each other by means of a flexible string made of an elastic or non-elastic material; a flexible disc disposed at a junction of the flexible string with the T-fastener;
- an introducer needle for introducing the T-fastener assembly into a lumen of the gallbladder of the patient; the introducer needle having a sharp needle-like inner slotted end having a longitudinal slot of a predetermined length and an outer end having a first locking arrangement for locking the introducer needle inside the introducer sheath; a magnet disposed about the longitudinal slot for magnetically holding the T-fastener in a longitudinal orientation inside the introducer needle and the anchor attached with the flexible siring lying outside the introducer needle but disposed inside the introducer sheath in a predefined orientation;
- the first locking arrangement comprising a first semi-circular flange on the introducer needle and a first pivoting hook formed on an arm pivotable about a first pivot point on the first semi-circular flange to lock or unlock the first pivoting hook on or from a predefined position provided on the expanded cylindrical disc of the introducer sheath to lock the introducer needle; the introducer needle completely removable from the introducer sheath by releasing the first pivoting hook from the expanded cylindrical disc of the introducer sheath;
- a T-fastener pusher disposed inside the introducer needle;
- a second locking arrangement comprising a second semi-circular flange formed on the T-fastener pusher and a second pivoting hook formed on an arm pivotable about a second pivot point on the second semi-circular flange to lock or unlock the second pivoting hook on or from a predefined position provided on the first semi-circular flange of the introducer needle to lock the T-fastener pusher; the T-fastener pusher completely removable from the introducer needle by releasing the pivoting hook of the T-pusher from the first semi-circular flange of the introducer needle;
- a grasper for grasping the shank of the anchor inside the introducer sheath in a predefined orientation; the grasper includes a longitudinal shaft having a pair of handles at an outer end thereof and a pair of grasping jaws at an outer surface of the longitudinal shaft and a pair of jaws for holding the shank of the anchor firmly in position inside the introducer sheath; the pair of grasping jaws grasps or releases the shank of the anchor of the T-fastener assembly by means of a pawl and ratchet mechanism provided on the grasper handles;
- a holding mechanism provided on the introducer sheath for holding the grasper in a predetermined position inside the introducer sheath; the holding mechanism comprises a holder having a first end pivotable about a pivot point provided on the expanded cylindrical disc and a second free end having at least one locking tab for locking or unlocking the holder into or from the at least one notch provided on the outer surface of the longitudinal shaft of the grasper; and
- a blocker to block an opening in the washer configured for the introducer needle after removing the introducing needle out of the introducer sheath; wherein the T-fastener assembly is inserted inside the introducer needle and the flexible string emerging through the slotted end thereof, to locate the shank and the plurality of flukes outside the introducer needle but within he introducer sheath.

* * * * *